United States Patent
Kataoka et al.

(10) Patent No.: US 6,905,744 B1
(45) Date of Patent: Jun. 14, 2005

(54) MULTILAYERED FILM AND CONTAINER

(75) Inventors: Tamotsu Kataoka, Naruto (JP);
Takayuki Denpou, Naruto (JP);
Motoaki Suzaki, Komatsushima (JP);
Tatsuya Tanaka, Naruto (JP);
Shigetoshi Kashiyama, Naruto (JP)

(73) Assignee: Otsuka Pharmaceutical Factory, Inc., Tokushima (JP)

(*) Notice: Subject to any disclaimer, the term of this patent is extended or adjusted under 35 U.S.C. 154(b) by 0 days.

(21) Appl. No.: 09/857,898

(22) PCT Filed: Dec. 9, 1999

(86) PCT No.: PCT/JP99/06932

§ 371 (c)(1),
(2), (4) Date: Jun. 13, 2001

(87) PCT Pub. No.: WO00/35673

PCT Pub. Date: Jun. 22, 2000

(30) Foreign Application Priority Data

Dec. 14, 1998 (JP) ............................................. 10-354913

(51) Int. Cl.$^7$ .......................... B29D 22/00; B29D 23/00; B32B 1/08
(52) U.S. Cl. .................... 428/35.7; 428/36.91; 428/218; 428/340; 428/515; 428/516; 428/523; 428/525
(58) Field of Search ............................ 428/35.7, 36.91, 428/515, 516, 523, 525, 218, 340, 545; 206/219

(56) References Cited

U.S. PATENT DOCUMENTS

| | | | | |
|---|---|---|---|---|
| 4,961,495 A | * | 10/1990 | Yoshida et al. | 206/219 |
| 5,478,617 A | * | 12/1995 | Watanabe et al. | 428/35.2 |
| 5,792,526 A | * | 8/1998 | Watanabe et al. | 428/35.7 |

FOREIGN PATENT DOCUMENTS

| | | |
|---|---|---|
| EP | 0 699 521 B1 | 3/1996 |
| JP | 62-64363 | 3/1987 |
| JP | 63-248633 | 10/1988 |
| JP | 03-277365 | 12/1991 |
| JP | 04-266759 | 9/1992 |
| WO | WO 99/03679 | 1/1999 |

* cited by examiner

Primary Examiner—Sandra M. Nolan
Assistant Examiner—Catherine A. Simone
(74) Attorney, Agent, or Firm—Finnegan, Henderson, Farbow, Garrett & Dunner, L.L.P.

(57) ABSTRACT

A multilayered film comprising five layers in which the first, third and fifth layers are made of an ethylene.α-olefin copolymer having a density of 0.930 to 0.950 g/cm$^3$ and the second and fourth layers are made of a mixed resin comprising 35 to 55% by weight of polypropylene having a density of 0.900 to 0.930 g/cm$^3$, 40 to 60% by weight of ethylene.α-olefin elastomer having a density of 0.860 to 0.900 g/cm$^3$, and 2 to 8% by weight of high-density polyethylene having a density of 0.955 to 0.970 g/cm$^3$; and a container made of the film (bag for infusion fluid, etc.). The multilayered film and the container are useful in medical applications.

8 Claims, 2 Drawing Sheets

MULTILAYERED FILM AND CONTAINER

TECHNICAL FIELD

The present invention relates to a multilayered film, and a container formed by using the same and, more particularly, to a multilayered film used particularly as a material for containing drug solution, blood, etc. in the medical field, and a container.

BACKGROUND ART

In order to improve properties of medical flexible plastic containers such as bag for infusion fluid, trials of employing a multilayered film as a material have been made. Examples of a conventional multilayered container include those made of a polyethylene resin described below.

1) Japanese Laid-Open Patent Publication No. 62-64363

A three-layer bag made of a linear low-density polyethylene, wherein the density of inner/outer layers is not less than 0.920 g/cm$^3$ and that of an intermediate layer is smaller than 0.920 g/cm$^3$.

2) Japanese Laid-Open Patent Publication No. 63-248633

A three-layer container made of a linear low-density polyethylene, wherein the density of inner/outer layers is from 0.910 to 0.940 g/cm$^3$ and that of an intermediate layer is from 0.880 to 0.905 g/cm$^3$ and, furthermore, a difference in density between the both layers is not less than 0.01 g/cm$^3$.

3) Japanese Laid-Open Patent Publication No. 3-277365

A three-layer bag wherein an outer layer is made of a linear low-density polyethylene having a density of not less than 0.920 g/cm$^3$ and an intermediate layer is made of a linear low-density polyethylene having a density of not more than 0.915 g/cm$^3$ and, furthermore, an inner layer is made of a branched low-density polyethylene having a density of not less than 0.918 g/cm$^3$.

4) Japanese Laid-Open Patent Publication No. 4-266759

A three or more-layer bag wherein an outer/inner layer is made of a resin prepared by mixing a linear branched low-density polyethylene having a density of not more than 0.930 g/cm$^3$ with 5 to 40% of a high-density polyethylene having a density of not less than 0.945 g/cm$^3$ and an intermediate layer is made of a resin prepared by mixing a linear low-density polyethylene having a density of not more than 0.920 g/cm$^3$ with 15% or less of the above-described high-density polyethylene.

However, the above-described conventional medical multilayered containers have some of the following drawbacks.

(i) Since the inner/outer layers of the film are composed of a polyethylene resin having a low-density, the heat resistance is not sufficient and seal and drop strengths are lowered by sterilization under high-temperature conditions, such as steam sterilization under high pressure, hot-water sterilization or the like.

(ii) After the completion of the sterilization under high-temperature condition, blocking is liable to be caused (low blocking resistance).

(iii) The wall thickness must be increased because of low strength of the film.

(iv) The rate of producing the bag can not be increased because of insufficient tensile strength of the film.

(v) Since the temperature of a heater can not be increased on heat sealing, sealing can not be conducted in a short time (low sealability).

(vi) The transparency and flexibility of the film are lowered after the completion of the sterilization.

In case a medical container (bag for infusion fluid) 10 shown in FIG. 1 is produced, two films 22 are laid one upon another and then the periphery of the film 22 is heat-sealed in the state where a port member (port) 20 is interposed between two films 22.

However, as shown in FIG. 2, the film 22 bends largely at the portion adjacent to the port member 20. Therefore, when a conventional multilayered film is heat-sealed, the film is stretched at the bend portion 24, and film thickness is reduced, so pinholes are likely to occur.

Therefore, an object of the present invention is to provide a multilayered film which is superior in heat resistance, blocking resistance, strength, sealability, transparency and flexibility, and which is capable of preventing pinholes from occurring at the bend portion on heat sealing.

DISCLOSURE OF INVENTION

Prosecuting their intensive studies to solve the above problems, the present inventors have studied intensively about a combination of a resin or mixed resin constituting each layer and a layer configuration of the whole multilayered film wherein an intermediate layer has a three-layer structure. As a result, they have found a novel combination of a resin composition and its configuration, which is capable of improving the heat resistance without impairing basic properties such as transparency, flexibility and the like, and completed the present invention.

That is, the present invention provides a multilayered film comprising five layers, characterized in that a first layer and a fifth layer are made of (A) an ethylene.α-olefin copolymer having a density of 0.930 to 0.950 g/cm$^3$; a second layer is made of (B) a mixed resin comprising 30 to 60% by weight of an ethylene.α-olefin copolymer having a density of 0.910 to 0.930 g/cm$^3$, 35 to 65% by weight of an ethylene.α-olefin elastomer having a density of 0.860 to 0.900 g/cm$^3$ and 1 to 10% by weight of a high-density polyethylene having a density of 0.955 to 0.970 g/cm$^3$; or (C) a mixed resin comprising 35 to 55% by weight of a polypropylene having a density of 0.900 to 0.930 g/cm$^3$, 40 to 60% by weight of an ethylene.α-olefin elastomer having a density of 0.860 to 0.900 g/cm$^3$ and 2 to 8% by weight of a high-density polyethylene having a density of 0.955 to 0.970 g/cm$^3$; a third layer is made of the ethylene.α-olefin copolymer (A); or (D) a mixed resin comprising 40 to 60% by weight of a polypropylene having a density of 0.900 to 0.930 g/cm$^3$ and 40 to 60% by weight of an ethylene.α-olefin elastomer having a density of 0.860 to 0.900 g/cm$^3$; and a fourth layer is made of the mixed resin (C).

According to the multilayered film of the present invention, it is possible to sufficiently prevent pinholes from occurring in the production of the above-described medical container (bag for infusion fluid) 10. Particularly, thermal fusion of the port 20 can be conducted at a relatively high temperature and the film does not stretch excessively at the bend portion 24; therefore, it is possible to securely prevent pinholes from occurring at the bend portion 24.

DESCRIPTION OF REFERENCE NUMERALS

Figure 1:
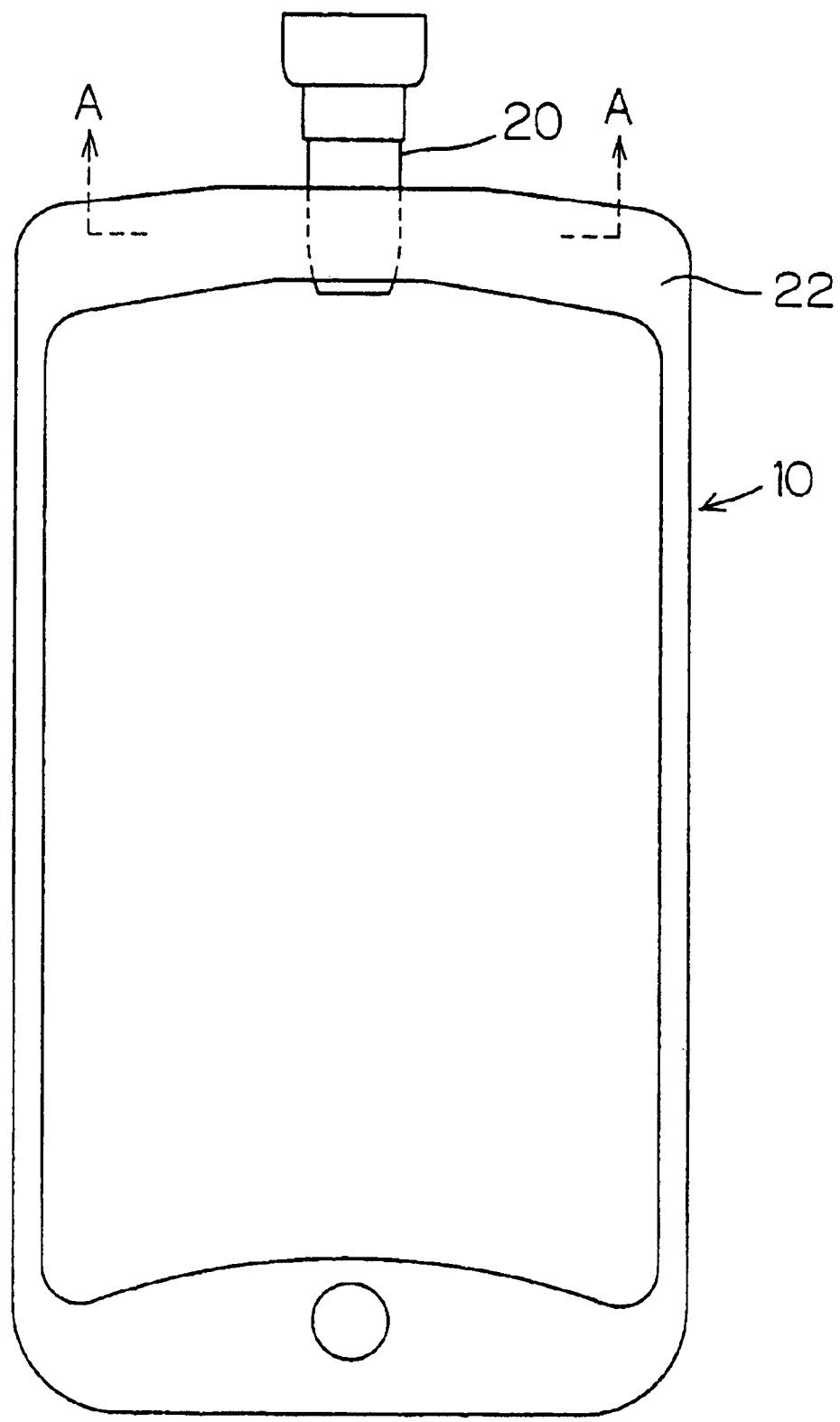
FIG. 1 is a front elevation view showing one embodiment of the container of the present invention.
Figure 2:
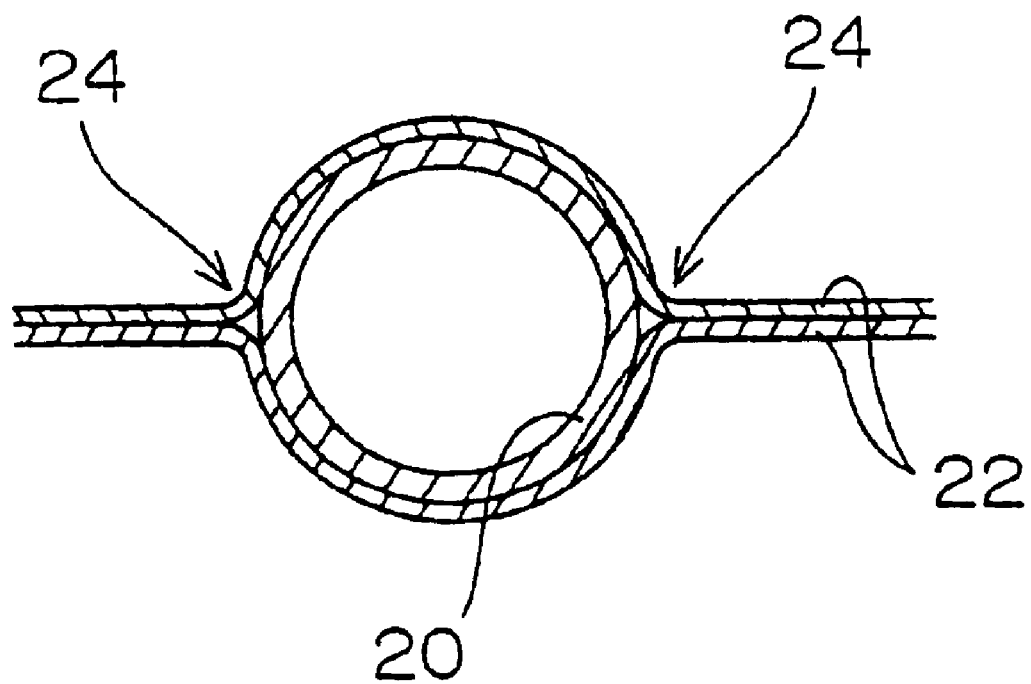
FIG. 2 is a fragmentary cross sectional view taken along lines A—A of FIG. 1.

10: Container
20: Port member

BEST MODE FOR CARRYING OUT THE INVENTION

The multilayered film of the present invention is preferably a multilayered film wherein the second layer is made of the mixed resin (C) and the third layer is made of the ethylene.α-olefin copolymer (A) in view of the purpose of reducing the production cost with maintaining sufficient heat resistance.

In the multilayered film of the present invention, the polypropylene used in the mixed resin (C) or (D) preferably has a melt flow rate (MFR) of 1 to 40 g/10 minutes (230° C.) and a melting point of 140 to 170° C., in view of the affinity for the other resin.

The proportion of thickness of each layer is preferably within the following range based on the whole thickness of the film, that is, the proportion of the first layer is from 5 to 15%, that of the second layer is from 25 to 45%, that of the third layer is from 2 to 15%, that of the fourth layer is from 25 to 45%, and that of the fifth layer is from 7 to 20%. More preferably, the proportion of the first layer is from 5 to 10%, that of the second layer is from 30 to 45%, that of the third layer is from 2 to 10%, that of the fourth layer is from 30 to 45%, and that of the fifth layer is from 7 to 15%.

The container of the present invention is characterized by using any of the above multilayered films and comprising the first and fifth layers as an outer and inner layers, respectively.

The container of the present invention is superior in heat resistance, blocking resistance, strength, sealability, flexibility and transparency and is capable of sufficiently preventing pinholes from generating because the container is formed by using the multilayered film of the present invention.

The resins of the respective layers in the multilayered film and container according to the present invention, and the method of producing the multilayered film and container according to the present invention will be described in detail, hereinafter.

Any value of physical properties defined in the present invention is based on the provision of The American Society for Testing and Materials (ASTM). The density, melt flow rate (MFR) and melting point are respectively measured according to ASTM D1505, ASTM D1238 and ASTM D2117.

First, the resins, copolymers and elastomers used in the multilayered film of the present invention will be described.
[Ethylene.α-olefin Copolymer and Ethylene.α-olefin Elastomer]

The α-olefin in the titled copolymer or elastomer includes, for example, α-olefin having 3 to 12 carbon atoms, such as propylene, 1-butene, 1-pentene, 1-hexene, 4-methyl-1-pentene, 1-heptene, 1-octene, 1-nonene, 1-decene, 1-undecene, 1-dodecene or the like.

As the titled copolymer or elastomer, for example, there can be preferably used those, wherein a branched chain is a single chain, produced by a low/moderate pressure method.
[High-density Polyethylene]

The titled high-density polyethylene may also be a copolymer with α-olefin, besides a homopolymer of ethylene. The α-olefin includes the above-described α-olefin having 3 to 12 carbon atoms. The amount of the α-olefin is not specifically limited, but is usually set within a range from 0.1 to 5 mol %.

The high-density polyethylene used in the present invention has a density within a range from 0.955 to 0.970 g/cm$^3$, and those having MFR of 1 to 30 g/10 minutes (190° C.) are particularly preferred.

[Polypropylene]

The titled polypropylene may also be a copolymer containing a small amount of ethylene or α-olefin, besides a homopolymer of propylene. The α-olefin includes, for example, the above described α-olefin having about 4 to 12 carbon atoms, such as 1-butene. The amount of the α-olefin is usually set to 10% by weight or less.

The polypropylene used in the present invention has a density within a range from 0.900 to 0.930 g/cm$^3$, and an isotactic polypropylene having MFR of 1 to 40 g/10 minutes (230° C.) and a melting point within a range from 140 to 170° C. is particularly preferred.

The mixed resin constituting the multilayered film of the present invention will be described below.

[Mixed resin comprising 30 to 60% by weight of an ethylene.α-olefin copolymer having a density of 0.910 to 0.930 g/cm$^2$, 35 to 65% by weight of an ethylene.α-olefin elastomer having a density of 0.860 to 0.900 g/cm$^2$, and 1 to 10% by weight of a high-density polyethylene having a density of 0.955 to 0.970 g/cm$^2$ (mixed resin (B))]

As the ethylene.α-olefin copolymer, ethylene.α-olefin elastomer and high-density polyethylene, which constitute the titled mixed resin (B), there can be those wherein the density is within the titled range.

It is particularly preferred that the ethylene.α-olefin copolymer has a density of 0.915 to 0.925 g/cm$^3$ within the titled range. MFR is preferably from 1.0 to 5.0g/10 minutes (190° C.) and the melting point is preferably from 115 to 125° C.

It is particularly preferred that the ethylene.α-olefin elastomer has a density of 0.870 to 0.890 g/cm$^3$ within the titled range. MFR is preferably from 0.1 to 2.0 g/10 minutes (190° C.).

It is preferred that the high-density polyethylene has MFR of 1 to 30 g/10 minutes (190° C.)

It is preferred that the proportion of the ethylene.α-olefin copolymer, ethylene.α-olefin elastomer and high-density polyethylene, which constitute the titled mixed resin (B), is from 35 to 55% by weight, 40 to 60% by weight and 3 to 8% by weight, respectively.

When the proportion of the respective resins constituting the titled mixed resin (B) is not within the above range, there arise problems such as deterioration of the flexibility, heat resistance, formability and pinhole resistance.

[Mixed resin comprising 35 to 55% by weight of a polypropylene having a density of 0.900 to 0.930 g/cm$^2$, 40 to 60% by weight of an ethylene.α-olefin elastomer having a density of 0.860 to 0.900 g/cm$^2$, and 2 to 8% by weight of a high-density polyethylene having a density of 0.955 to 0.970 g/cm$^2$ (mixed resin (C))]

As the polypropylene, ethylene.α-olefin elastomer and high-density polyethylene, which constitute the titled mixed resin (C), there can be those wherein the density is within the titled range.

It is particularly preferred that the polypropylene is an isotactic polypropylene having MFR of 1 to 40 g/10 minutes (230° C.) and a melting point within a range from 140 to 170° C., among those having a density within the titled range.

Preferred range of the density, MFR or melting point of the ethylene.α-olefin elastomer and high-density polyethylene is the same as that described above.

It is preferred that the proportion of the polypropylene, ethylene.α-olefin elastomer and high-density polyethylene, which constitute the titled mixed resin (C), is respectively from 40 to 50% by weight, 45 to 55% by weight and 3 to 7% by weight, within the titled range.

When the proportion of the respective resins constituting the titled mixed resin (C) is not within the above range, there arise problems such as deterioration of the flexibility, heat resistance, formability and pinhole resistance.

Particularly, when the proportion of the high-density polyethylene exceeds the above range, it becomes impossible to obtain a film because of difficulty in forming. On the other hand, when the proportion is smaller than the above range, there arise problems on appearance, such as a lot of wrinkles that are formed on a container formed by using a multilayered film.

[Mixed resin comprising 40 to 60% by weight of a polypropylene having a density of 0.900 to 0.930 g/cm$^2$ and 40 to 60% by weight of an ethylene.α-olefin elastomer having a density of 0.860 to 0.900 g/cm$^2$ (mixed resin (D))]

As the polypropylene and ethylene.α-olefin elastomer, which constitute the titled mixed resin (D), there can be those wherein the density is within the titled range.

Preferred range of the density, MFR or melting point of the polypropylene and ethylene.α-olefin elastomer is the same as that described above.

It is preferred that the proportion of the polypropylene and ethylene.α-olefin copolymer, which constitute the titled mixed resin (D), is respectively from 40 to 50% by weight and 50 to 60% by weight, within the titled range.

When the proportion of the respective resins constituting the titled mixed resin (D) is not within the above range, there arise problems such as lowering of the strength and deterioration of the pinhole resistance.

The respective layers of the multilayered film of the present invention will be described below.

[First Layer and Fifth Layer]

The first layer and fifth layer respectively function as an outer layer and an inner layer of the medical container. The mechanical strength (particularly tensile strength) and heat resistance are required to the first layer (outer layer), while the sealability and blocking resistance are required to the fifth layer (inner layer).

As the first layer and fifth layer, for example, an ethylene.α-olefin copolymer having a density of 0.930 to 0.950 g/cm$^3$ as a resin having the above-described properties is used.

Among the above-described copolymers, those having a density of 0.935 to 0.945 g/cm$^3$, MFR of 1.0 to 5.0 g/10 minutes (190° C.) and a melting point of 120 to 130° C. are further superior in the above-described properties, which are used more preferably.

The proportion of the thickness of the first layer (outer layer) is preferably from 5 to 15%, and more preferably from 5 to 10%, based on the thickness of the whole film. When the proportion of the thickness of the first layer is smaller than the above range, there are fears that the mechanical strength and heat resistance of the multilayered film and medical container become insufficient. On the other hand, even if the proportion exceeds the above range, the mechanical strength and heat resistance do not change greatly and the flexibility of the multilayered film is likely to be lowered instead.

On the other hand, the proportion of the thickness of the fifth layer (inner layer) is preferably from 7 to 20%, and more preferably from 7 to 15%, based on the thickness of the whole film. When the proportion of the thickness of the fifth layer is smaller than the above range, the sealability of the multilayered film is lowered and the appearance of the container is likely to become inferior. On the other hand, even if the proportion exceeds the above range, the sealability and blocking resistance do not change greatly and the flexibility of the multilayered film is likely to be lowered instead.

[Second Layer]

The second layer in the multilayered film of the present invention is one of three intermediate layers, and the above-described mixed resin (B) or (C) is used to impart the flexibility without impairing the heat resistance of the multilayered film.

The proportion of the thickness of the second layer is preferably from 25 to 45%, and more preferably from 30 to 45%, based on the thickness of the whole film. When the proportion of the thickness is not within the above range, there are fears that the flexibility of the multilayered film and container becomes insufficient and the heat resistance and pinhole resistance are lowered.

[Third Layer]

The third layer in the multilayered film of the present invention is a layer located at the most center position among three intermediate layers, and the ethylene.α-olefin copolymer (A) used in the first layer and fifth layer, or the mixed resin (D) is used to maintain the strength of the multilayered film.

The proportion of the thickness of the third layer is preferably from 2 to 15% based on the thickness of the whole film. When the proportion of the thickness is not within the above range, there is a fear that the strength of the multilayered film and container becomes insufficient, or the flexibility is impaired even if the strength is maintained.

[Fourth Layer]

The fourth layer in the multilayered film of the present invention is one of three intermediate layers, and the above-described mixed resin (C) is used to impart the heat resistance with maintaining the flexibility of the multilayered film.

The proportion of the thickness of the fourth layer is preferably from 25 to 45%, and more preferably from 30 to 45%, based on the thickness of the whole film. When the proportion of the thickness is not within the above range, the same problem as in case of the above-described second layer arises.

According to the multilayered film of the present invention, it becomes possible to maintain the strength of the whole film with maintaining the flexibility (elasticity) of the whole film by setting the layer configuration, particularly configuration of the intermediate layers (second to fourth layers), thereby making it possible to further improve the heat resistance.

Accordingly, there can be provided a container which can stand against the pinhole test and drop test under severe conditions.

The method of producing the multilayered film of the present invention will be described below.

In order to produce the multilayered film of the present invention, for example, a water-cooling or air-cooling coextrusion inflation method, a coextrusion T-die method, a dry lamination method and an extrusion lamination method can be used. In view of performances, particularly transparency, economy and sanitation, a water-cooling coextrusion inflation method and a coextrusion T-die method are preferably used.

It is necessary that any method is carried out at the temperature at which the resins of the respective layers are molten. When the temperature is raised too much, heat deterioration occur in a portion of the resin, whereby deterioration in performance may be caused by the deteriorated substance. Accordingly, the temperature on production of the multilayered film of the present invention is usually set within a range from 150 to 250° C., and preferably from 170 to 200° C.

The thickness of the film of the present invention thus produced is generally from 100 to 350 μm, and preferably from 200 to 300 μm, but can be varied appropriately depending on the purposes. Even a film having a thickness of only about 250 μm maintains sufficient strength.

The container of the present invention will be described below with reference to FIG. 1 showing one embodiment of the container.

FIG. 1 is a front elevation view showing one embodiment of a medical container (bag for infusion fluid).

A medical container 10 having a predetermined shape and size is produced by cutting two sheet-like multilayered films obtained in the above-described procedure using a normal method, laying the respective fifth layers one upon another as an inner layer, heat-sealing the periphery of the container 10, and attaching a port member 20 using a means such as heat sealing. The container 10 may also be formed by heat sealing after the multilayered film is formed into a tube with the fifth layer inside. As the conditions for heat sealing of the film, the temperature within a range from 130 to 200° C. can be employed. In the case of the film having a thickness of about 250 μm, sealing can be conducted in a short time such as about 0.5 to 6 seconds within the above temperature range.

It is preferred to use, as a port member 20, a resin having excellent fusibility with the fifth layer in the multilayered film of the present invention, e.g. those made of polyethylene. In case of the port member 20 made of polyethylene having a melting point of about 120 to 130° C., heat sealing may be conducted by pre-heating the port member for several seconds and heating at about 140 to 170° C. for about 0.5 to 5 seconds.

EXAMPLES

The following Examples, Comparative Examples and Test Examples illustrate the multilayered film and container of the present invention.

The components constituting the mixed resins used in Examples and Comparative Examples are as follows.
[Ethylene.α-olefin Copolymer]

(1) Ethylene.1-butene copolymer [manufactured by MITSUI CHEMICALS, INC., density=0.920 g/cm$^3$, MFR=2.1 g/10 minutes (190° C.)]
[Ethylene.α-olefinic Elastomer]

(2) Ethylene.1-butene copolymer elastomer [manufactured by MITSUI CHEMICALS, INC., density= 0.885 g/cm$^3$, MFR=0.5 g/10 minutes (190° C.)]
[High-density Polyethylene]

(3) Ethylene.1-butene copolymer [manufactured by MITSUI CHEMICALS, INC., density=0.962 g/cm$^3$, MFR=15 g/10 minutes (190° C.)]
[Polypropylene]

(4) Isotactic polypropylene (ethylene content: 5% by weight or less) [manufactured by MITSUI CHEMICALS, INC., density=0.910 g/cm$^3$, MFR=1.6 g/10 minutes (230° C.)]

The resins shown in Table 1 are as follows.
[Ethylene.α-olefin Copolymer (A)]

A-1: Ethylene.1-butene copolymer [manufactured by MITSUI CHEMICALS, INC., density=0.940 g/cm$^3$, MFR= 2.1 g/10 minutes (190° C.)]
[Mixed Resin (B)]

B-1: Mixed resin comprising 45% by weight of the copolymer (1), 50% by weight of the elastomer (2) and 5% by weight of the high-density polyethylene (3) (density of mixed resin=0.906 g/cm$^3$)

[Mixed Resin (C)]

C-1: Mixed resin comprising 45% by weight of the polypropylene (4), 50% by weight of the elastomer (2) and 5% by weight of the high-density polyethylene (3).

C-2: Mixed resin comprising 41.5% by weight of the polypropylene (4), 53.5% by weight of the elastomer (2) and 5% by weight of the high-density polyethylene (3). C-3: Mixed resin comprising 30% by weight of the polypropylene (4), 65% by weight of the elastomer (2) and 5% by weight of the high-density polyethylene (3).

C-4: Mixed resin comprising 45% by weight of the polypropylene (4), 45% by weight of the elastomer (2) and 10% by weight of the high-density polyethylene (3).
[Mixed Resin (D)]

D-1: Mixed resin comprising 45% by weight of the polypropylene (4) and 55% by weight of the elastomer (2)

Examples 1 to 5 and Comparative Examples 1 to 4 (Production of Multilayered Film) Using the resins (mixed resin) A-1, B-1, C-1 to C-4 and D-1, films having the following layer configuration shown in the following Table 1 were respectively produced by a water-cooling coextrusion inflation method.

The multilayered film of Comparative Example 2 was a four-layer film which has not a layer corresponding to the third layer.

In Comparative Example 4 wherein the composition of the mixed resin (C) used in the second and fourth layers as the intermediate layer, a film could not be obtained because of difficulty in forming.

TABLE 1

Upper column: Kind of resin, Lower column: Thickness

| | First layer | Second layer | Third layer | Fourth layer | Fifth layer |
|---|---|---|---|---|---|
| Example 1 | A-1 | B-1 | A-1 | C-1 | A-1 |
| | 20 μm | 100 μm | 10 μm | 100 μm | 30 μm |
| Example 2 | A-1 | C-1 | A-1 | C-1 | A-1 |
| | 20 μm | 100 μm | 10 μm | 100 μm | 30 μm |
| Example 3 | A-1 | B-1 | D-1 | C-1 | A-1 |
| | 20 μm | 95 μm | 20 μm | 95 μm | 30 μm |
| Example 4 | A-1 | C-2 | A-1 | C-2 | A-1 |
| | 20 μm | 100 μm | 10 μm | 100 μm | 30 μm |
| Example 5 | A-1 | C-1 | D-1 | C-1 | A-1 |
| | 20 μm | 95 μm | 20 μm | 95 μm | 30 μm |
| Comp. Example 1 | A-1 | D-1 | A-1 | D-1 | A-1 |
| | 20 μm | 100 μm | 10 μm | 100 μm | 30 μm |
| Comp. Example 2 | A-1 | B-1 | — | C-1 | A-1 |
| | 30 μm | 100 μm | | 100 μm | 30 μm |
| Comp. Example 3 | A-1 | C-3 | A-1 | C-3 | A-1 |
| | 20 μm | 100 μm | 10 μm | 100 μm | 30 μm |
| Comp. Example 4 | A-1 | C-4 | D-1 | C-4 | A-1 |
| | 20 μm | 95 μm | 20 μm | 95 μm | 30 μm |

(Production of Container)

Using the films of Examples 1 to 5 and Comparative Examples 1 to 4, medical containers (bags for infusion fluid) 10 having a volume of 500 ml shown in FIG. 1 were produced. Heat sealing of the peripheral portion in the forming of the medical container 10 was conducted at 155° C. for 4.5 seconds, while sealing of a port member 20 was conducted at 140 to 150° C. for 3 seconds.
(Performance Test)

Test Example 1

With respect to the medical containers (bag for infusion fluids) 10 obtained by using the multilayered films of Examples 1 to 5, the evaluation tests of various characteristics were conducted by the following procedure.

Heat resistance: Each container was filled with distilled water. After it is subjected to steam sterilization under high pressure at 110° C. for 40 minutes, the state of deformation, fracture and seal leakage of the container was visually observed.

Drop test: Each container was kept in cold storage at about 4° C. After it is dropped five times from three directions and from a height of 1 meter, the state of fracture and seal leakage of the container was visually observed.

Flexibility: Natural drainage of a solution contained in each container was visually observed.

Transparency: Each container was filled with distilled water and, after subjected to steam sterilization under high pressure in the same manner as that described above, the container was visually observed and the transmittance of light with 450 nm was measured.

Appearance: Each container was visually observed to examine the state of wrinkle, blocking, deformation and fracture.

In the evaluation of the heat resistance, drop test, flexibility, transparency and appearance, symbols ⊙, ○, ∆ and X show "Very good", "Good (suited for practical use)", "Slightly poor (unsuited for practical use)" and "Poor", respectively.

The above test results are shown in Table 2.

TABLE 2

|  | Example 1 | Example 2 | Example 3 | Example 4 | Example 5 |
|---|---|---|---|---|---|
| Heat resistance | ⊙ | ⊙ | ⊙ | ⊙ | ⊙ |
| Drop test | ⊙ | ⊙ | ⊙ | ⊙ | ⊙ |
| Flexibility | ⊙ | ⊙ | ⊙ | ⊙ | ⊙ |
| Transparency |  |  |  |  |  |
| Visual evaluation | ⊙ | ⊙ | ⊙ | ⊙ | ⊙ |
| Transmittance (%) | 83.2 | 83.4 | 85.3 | 85.7 | 88.0 |
| Appearance | ⊙ | ⊙ | ⊙ | ⊙ | ⊙ |

As is apparent from the results of Table 2, the containers of the present invention exhibited very good results in all properties of the heat resistance, drop test, flexibility, transparency and appearance.

Test Example 2

Each of the medical containers (bag for infusion fluids) 10 obtained by using the multilayered films of Examples 1 to 5 and Comparative Examples 1 to 3 was filled with physiologic saline, sealed with a rubber stopper, and then subjected to steam sterilization under high pressure at 110° C. for 40 minutes. After the completion of the treatment, it was examined whether pinholes were present or not, using a handy electrostatic capacity type pinhole tester [pinhole tester, Model H, manufactured by Densoku Seiko Co., Ltd.].

With respect to the containers wherein sealing of the port member 20 was conducted under three conditions of the temperature of 140, 145 and 150° C., the examination was conducted under three conditions of the applied voltage of 15, 20 and 25 kV, using ten bags for each condition. That is, 90 bags were examined in total.

The above test was conducted under considerably severe conditions as compared with normal production conditions. Accordingly, when the proportion of specimens wherein pinholes occurred was smaller than 5% (five or less specimens out of 90 specimens), the pinhole resistance was rated good.

The number of specimens wherein pinholes were found and respective proportions (%) are shown in Table 3.

TABLE 3

|  | Examples |  |  |  |  | Comp. Examples |  |  |
|---|---|---|---|---|---|---|---|---|
|  | 1 | 2 | 3 | 4 | 5 | 1 | 2 | 3 |
| Number of specimens | 4 | 1 | 4 | 3 | 4 | 0 | 9 | 15 |
| Proportion (%) | 4.4 | 1.1 | 4.4 | 3.3 | 4.4 | 0 | 10.0 | 16.7 |

As is apparent from Table 3, all containers of Examples 1 to 5 were superior in pinhole resistance because the proportion of specimens wherein pinholes were found is smaller than 5%.

To the contrary, the container of Comparative Example 2 made of a multilayered film comprising four layers and the container of Comparative Example 3 wherein the composition of the mixed resin (C) used in the second and fourth layers as the intermediate layer is not within the range of the present invention did not exhibit pinhole resistance sufficient for practical use because the proportion of specimens wherein pinholes were found is large.

The container of Comparative Example 1 wherein any of the mixed resins used in the second and fourth layers as the intermediate layer contains no high-density polyethylene was superior in pinhole resistance because the proportion of specimens wherein pinholes were found is 0%. However, the container was found to be unsuited as a medical container because appearance was very poor due to various wrinkles which occurred after the completion of the sterilization treatment.

In the present invention, films having each layer configuration shown in the following Table 4 can be formed in the same manner as in Examples 1 to 5. These films also have the same excellent properties as those described above.

TABLE 4

Upper column: Kind of resin, Lower column: thickness

|  | First layer | Second layer | Third layer | Fourth layer | Fifth layer |
|---|---|---|---|---|---|
| Example 6 | A-1 | B-1 | A-1 | C-2 | A-1 |
|  | 20 μm | 100 μm | 10 μm | 100 μm | 30 μm |
| Example 7 | A-1 | B-1 | D-1 | C-2 | A-1 |
|  | 20 μm | 100 μm | 10 μm | 100 μm | 30 μm |
| Example 8 | A-1 | C-1 | A-1 | C-2 | A-1 |
|  | 20 μm | 100 μm | 10 μm | 100 μm | 30 μm |
| Example 9 | A-1 | C-1 | D-1 | C-2 | A-1 |
|  | 20 μm | 100 μm | 10 μm | 100 μm | 30 μm |
| Example 10 | A-1 | C-2 | A-1 | C-1 | A-1 |
|  | 20 μm | 100 μm | 10 μm | 100 μm | 30 μm |
| Example 11 | A-1 | C-2 | D-1 | C-1 | A-1 |
|  | 20 μm | 100 μm | 10 μm | 100 μm | 30 μm |
| Example 12 | A-1 | C-2 | D-1 | C-2 | A-1 |
|  | 20 μm | 100 μm | 10 μm | 100 μm | 30 μm |

Industrial Applicability

The multilayered film and container according to the present invention are superior in heat resistance, blocking resistance, strength, sealability, transparency, flexibility and appearance and have such an advantage that pinholes do not occur at the bend portion on heat sealing. Therefore, they can be suitably used as a medical container such as bag for infusion fluid, blood bag or the like.

What is claimed is:

1. A multilayered film comprising five layers, wherein:

a first layer and a fifth layer are made of (A) an ethylene.α-olefin copolymer having a density of 0.930 to 0.950 g/cm$^3$;

a second layer is made of:

(B) a mixed resin comprising 30 to 60% by weight of an ethylene α-olefin copolymer having a density of 0.910 to 0.930 g/cm$^3$, 35 to 65% by weight of an ethylene.α-olefin elastomer having a density of 0.860 to 0.900 g/cm$^3$ and 1 to 10% by weight of a high-density polyethylene having a density of 0.955 to 0.970 g/cm$^3$; or (C) a mixed resin comprising 35 to 55% by weight of a polypropylene having a density of 0.900 to 0.930 g/cm$^3$, 40 to 60% by weight of an ethylene.α-olefin elastomer having a density of 0.860 to 0.900 g/cm$^3$ and 2 to 8% by weight of a high-density polyethylene having a density of 0.955 to 0.970 g/cm$^3$;

a third layer is made of:

the ethylene.α-olefin copolymer (A); or (D) a mixed resin comprising 40 to 60% by weight of a polypropylene having a density of 0.900 to 0.930 g/cm$^3$ and 40 to 60% by weight of an ethylene.α-olefin elastomer having a density of 0.860 to 0.900 g/cm$^3$; and a fourth layer is made of:

(E) a mixed resin comprising 35 to 55% by weight of an isotactic polypropylene having a melt flow rate (MFR) of 1 to 40 g/10 minutes (230° C.) and a melting point of 140 to 170° C., 40 to 60% of an ethylene.1 butene elastomer having a density of 0.860 to 0.900 g/cm$^3$ and 2 to 8% of a high-density polyethylene having a density of 0.955 to 0.970 g/km$^3$.

2. The multilayered film according to claim 1, wherein the second layer is made of the mixed resin (C) and the third layer is made of the ethylene.α-olefin copolymer (A).

3. The multilayered film according to claim 1 or 2, wherein said polypropylene of mixed resin (C) is an isotactic polypropylene having a melt flow rate (MFR) of 1 to 40 g/10 minutes (230° C.) and a melting point of 140 to 170° C.

4. The multilayered film according to claim 1, wherein a proportion of each layer is within the following range based on the whole thickness of the film:

first layer; 5 to 15%;

second layer: 25 to 45%;

third layer: 2 to 15%;

fourth layer: 25 to 45%; and fifth layer: 7 to 20%.

5. The multilayered film according to claim 4, wherein a proportion of each layer is within the following range based on the whole thickness of the film:

first layer: 5 to 10%;

second layer: 30 to 45%;

third layer: 2 to 10%;

fourth layer: 30 to 45%; and fifth layer: 7 to 15%.

6. The multilayered film according to claim 4, wherein the thickness of the whole film is from 200 to 300 μm.

7. A container comprising the multilayered film according to claim 1, which container has the first layer of the multilayered film as an outer layer and the fifth layer as an inner layer.

8. The container according to claim 7, which is formed by interposing a port member made of polyethylene between the films and fusing them.

* * * * *

UNITED STATES PATENT AND TRADEMARK OFFICE
CERTIFICATE OF CORRECTION

PATENT NO.   : 6,905,744 B1
DATED        : June 14, 2005
INVENTOR(S)  : Tamotsu Kataoka et al.

It is certified that error appears in the above-identified patent and that said Letters Patent is hereby corrected as shown below:

Column 11,
Line 29, after "mixed resin", insert -- (C) --.

Column 12,
Line 4, "claim 1 or 2," should read -- claim 2, --.
Line 11, "first layer;" should read -- first layer: --.

Signed and Sealed this

Fourteenth Day of March, 2006

JON W. DUDAS
*Director of the United States Patent and Trademark Office*